(12) United States Patent
Whatley et al.

(10) Patent No.: US 6,452,158 B1
(45) Date of Patent: Sep. 17, 2002

(54) APPARATUS FOR DETERMINING THE POSITION OF A MOVABLE MECHANICAL ELEMENT AND METHOD OF MARKING A MECHANICAL ELEMENT

(75) Inventors: Mark Lewis Whatley, Eckington; John Shepherd, Little Haywood; Roger William Brassington; Ian Arnold Moore, both of Stoke-On-Trent, all of (GB)

(73) Assignee: J C Bamford Excavators Limited, Rocester (GB)

( * ) Notice: Subject to any disclaimer, the term of this patent is extended or adjusted under 35 U.S.C. 154(b) by 0 days.

(21) Appl. No.: 09/285,197

(22) Filed: Apr. 1, 1999

(30) Foreign Application Priority Data

Apr. 2, 1998 (GB) .............................................. 9807020

(51) Int. Cl.$^7$ ................................................. G01D 5/34
(52) U.S. Cl. ..................... 250/231.13; 356/617; 341/13
(58) Field of Search ...................... 250/231.13, 231.14, 250/231.18; 356/601, 614, 616, 617, 635; 341/9, 11, 13, 15

(56) References Cited

U.S. PATENT DOCUMENTS

| | | |
|---|---|---|
| 3,702,471 A | 11/1972 | Kennedy et al. |
| 3,746,842 A | 7/1973 | Fowler |
| 4,071,818 A | 1/1978 | Krisst |
| 4,074,258 A | 2/1978 | Dor″ et al. |
| 4,112,295 A | 9/1978 | Dubik et al. |
| 4,631,519 A | 12/1986 | Johnston |
| 4,668,862 A | 5/1987 | Waibel |
| 4,715,714 A | 12/1987 | Gaechter et al. |
| 4,756,229 A | 7/1988 | Drakeley |
| 4,901,073 A | 2/1990 | Kibrick |
| 4,922,077 A | 5/1990 | Gordon |
| 4,972,061 A | 11/1990 | Duley et al. |
| 5,138,560 A | 8/1992 | Lanfer et al. |
| 5,214,426 A | 5/1993 | Minohara et al. |
| 5,235,181 A | 8/1993 | Durana et al. |
| 5,239,177 A | 8/1993 | Cunniff |
| 5,371,598 A | 12/1994 | Ghaem et al. |
| 5,880,882 A | 3/1999 | Michel et al. |
| 6,147,342 A | * 11/2000 | Kucher .................. 250/231.13 |

FOREIGN PATENT DOCUMENTS

| | | |
|---|---|---|
| DE | 3035774 A1 | 5/1982 |
| DE | 31 16333 C2 | 11/1982 |
| DE | 3634730 A1 | 10/1986 |
| DE | 3818044 A1 | 11/1989 |
| EP | 0 039 921 A2 | 11/1981 |
| EP | 0 100 243 | 2/1984 |
| EP | 0 296808 | 12/1988 |
| EP | WO 89/07302 | 8/1989 |
| EP | 0 497 742 A1 | 8/1992 |
| EP | 0 503 716 A | 9/1992 |
| EP | 0 571 796 A | 12/1993 |
| EP | 0 638810 A1 | 2/1995 |

(List continued on next page.)

OTHER PUBLICATIONS

Digital displacement transducer using pseudo–random binary sequences and a microprocessor by B. E. Jones, Msc, PhD, Ceng, MIEE, MInstPet, and K. Zia, Bsc, Msc Trans Inst M C vol. 3, No. 1, Jan.–Mar. 1981, pp. 13–20 and pp. 368–379.

Laser surface treatment D.S. Gnanamuthu Optical Engineering/Sep./Oct. 1980/vol. 19 No. 5 pp. 783–792.

*Primary Examiner*—Kevin Pyo
(74) *Attorney, Agent, or Firm*—Marshall, Gerstein & Borun

(57) ABSTRACT

An apparatus for determining the position of a mechanical element wherein the mechanical element is marked in an optically readable manner, comprising reading means to provide a first output dependent on the position of the mechanical element.

42 Claims, 6 Drawing Sheets

FOREIGN PATENT DOCUMENTS

| | | |
|---|---|---|
| FR | 2 233 512 | 6/1973 |
| GB | 1 511 044 | 5/1978 |
| GB | 1 515 467 | 6/1978 |
| GB | 2 121 252 A | 12/1983 |
| GB | 2 297 840 A | 8/1996 |
| JP | 60 063416 A | 4/1985 |
| JP | 63-280435 | 11/1988 |
| WO | WO 93 20403 A | 10/1993 |
| WO | WO 93 25865 A | 12/1993 |
| WO | WO 95 01510 A | 1/1995 |

* cited by examiner

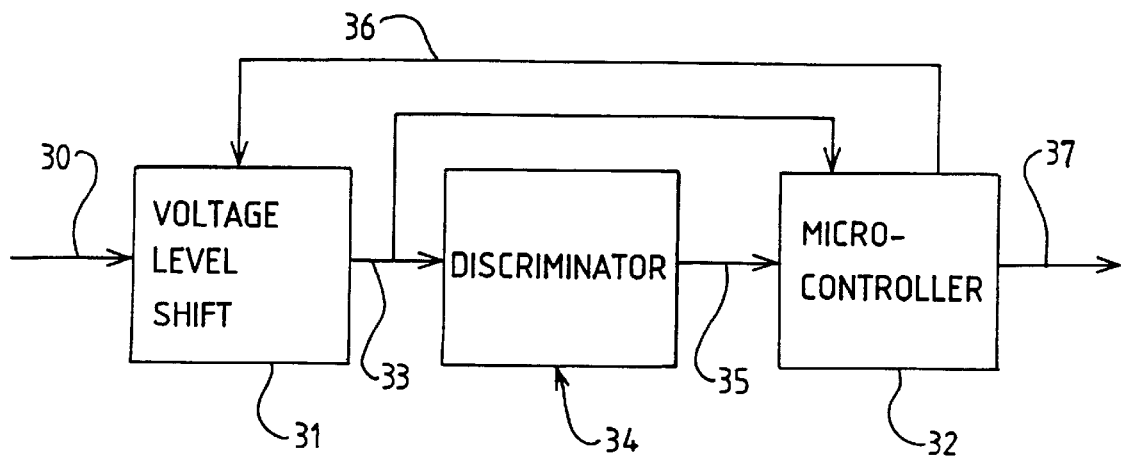
FIG 5
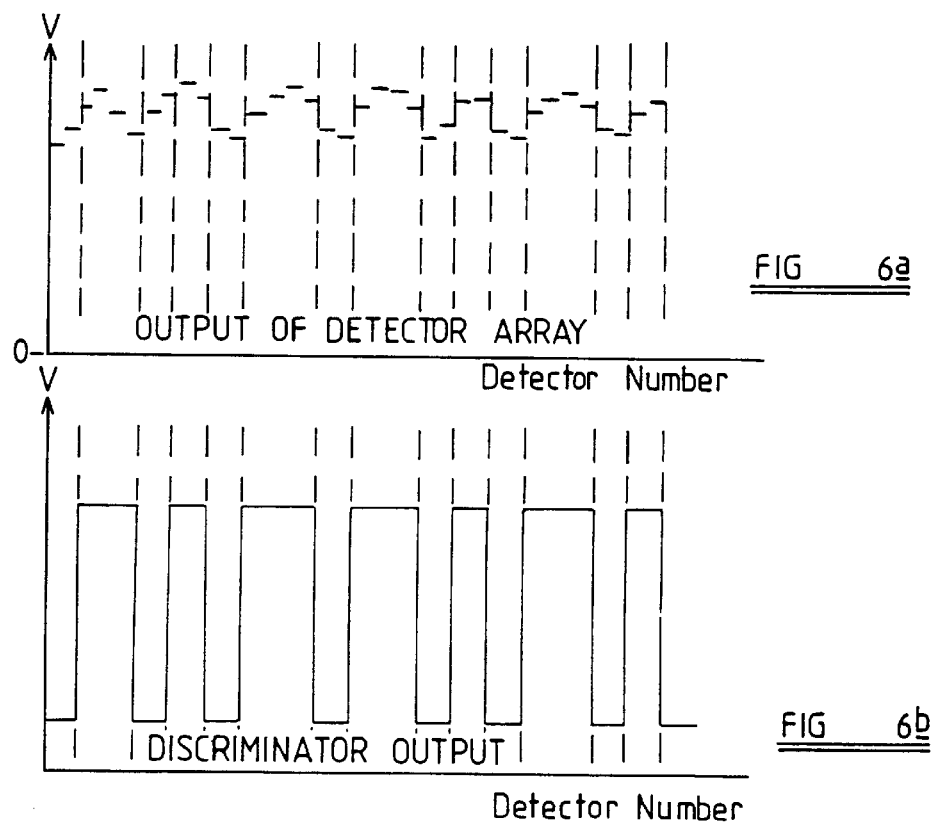
FIG 6a
FIG 6b

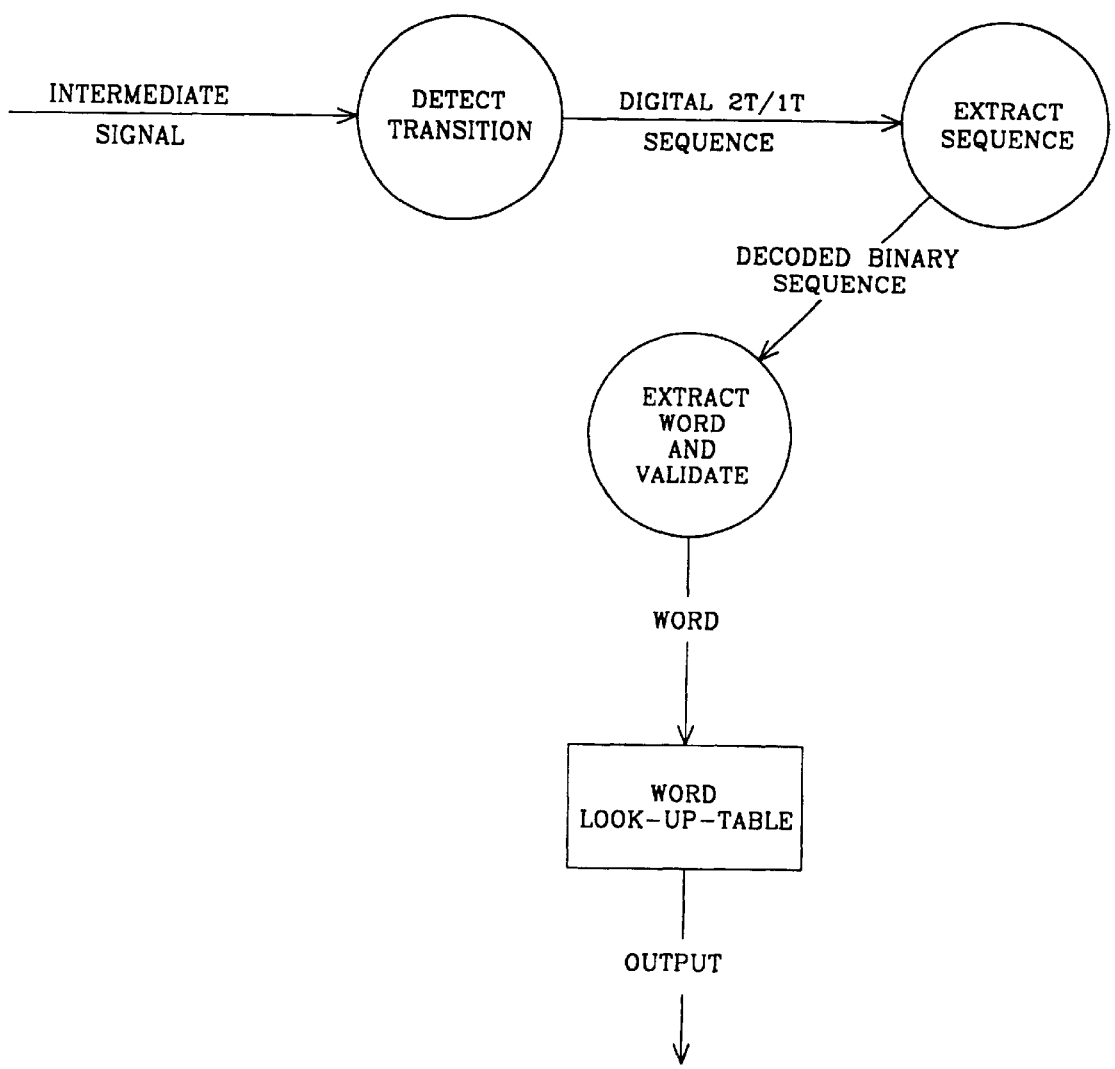

APPARATUS FOR DETERMINING THE POSITION OF A MOVABLE MECHANICAL ELEMENT AND METHOD OF MARKING A MECHANICAL ELEMENT

DESCRIPTION OF INVENTION

This invention is concerned with an apparatus for determining the position of a movable mechanical element and a method of marking a mechanical element, particularly but not exclusively for a mechanical element comprising a piston rod of a ram which is movable relative to a cylinder of the ram.

Means for detecting the position of a piston rod relative to a cylinder of a fluid operable ram are known, but rely on detecting the position of a device actuated by the ram by use of a sensor (such as a potentiometer) placed on the fulcrum of the device, and then inferring the position of the rod from a position of the device activated thereby. However, the rod position measurement obtained may be subject to mechanical deficiencies such as backlash between the rod and the actuated device. Such position detectors may also be mechanical and so are subject to deficiencies and wear themselves. Magnetic marking of a piston rod has been used to give a direct indication of the rod's position, but such magnetic systems are subject to electromagnetic interference and to demagnetisation of the marking.

It is known to provide optically readable marking on the surface of a mechanically element, and in particular to provide these markings by means of laser marking. However, such laser marking may impair the corrosion resistance of the rod.

It is an aim of the present invention to overcome or reduce at least one or more of the above problems.

According to one aspect of the present invention, we provide an apparatus for determining the position of a movable mechanical element wherein the mechanical element has a marking which is optically readable, the optically readable marking comprising at least part of the mechanical element with a surface having a first reflectivity and a plurality of areas having a second reflectivity, further comprising at least one of the following expedients;

a) said part of the mechanical element being provided with a substrate between the mechanical element and the surface.

b) said areas having a second reflectivity having a width which is generally constant in a direction parallel to the direction of movement of the mechanical element.

Where expedient a) is present, the substrate may be resistant to corrosion.

The substrate may be more resistant to laser marking than said surface having a first reflectivity.

The surface having a first reflectivity may comprise chrome.

The substrate may comprise bronze.

The bronze may comprise 88% to 92% copper and 12% to 8% tin.

The substrate may have a thickness in the range 0.038 mm to 0.051 mm.

The substrate may have a surface finish in the range 0.2 to 0.4 μm.

At least the part of the mechanical element to be provided with a substrate may have a surface finish of less than 0.8 μm.

The first reflectivity may be greater than the second reflectivity.

Where expedient b) is present, the marking may comprise a plurality of code elements, each comprising a plurality of said areas of second reflectivity.

Each code element may encode a numerical value in binary digits.

Each binary digit may be indicated by the distance between two of said areas having a second reflectivity.

Each code element may encode a unique number.

Each code element may comprise a unique part of a pseudorandom binary sequence.

The apparatus may further comprise reading means to provide an output dependent on the position of the mechanical element, said reading means comprising illuminating means, detector means and decoding means.

The illuminating means may comprise a light emitting diode.

The detector means may be disposed to detect light from the illuminating means reflected from said surface having a first reflectivity and said areas having a second reflectivity, the detector means comprising a detector which provides a signal having a value within a first range when light from a part of said surface having said first reflectivity is reflected thereon and having a valve within a second range when light from an area having said second reflectivity.

The detector means may comprise an array having a plurality of said detectors.

The array may provide an intermediate signal to said decoding means, said intermediate signal comprising a signal from each of said detectors.

The decoding means may comprise electronic means to decode said intermediate signal from said detector means to provide said output.

The decoding means may comprise means to detect a detector signal of the intermediate signal corresponding to a transition corresponding to an edge of an area of second reflectivity and means to identify a plurality of binary digits from the separation of a plurality of said transitions.

The decoding means may comprise means to identify a code element from said binary digits and provide said output indicating the position of the mechanical rod dependent on said code element.

The decoding means may further comprise means to identify the detector of the detector array on which a selected one of said transitions falls, to provide a fine position.

The apparatus may further comprise focusing means to focus light reflected from said surface said of mechanical element or said areas onto said detector means.

The mechanical element may comprise a piston rod of a fluid operated ram.

According to a second aspect of the invention, we provide a method of marking a mechanical element comprising the steps of providing a surface having a first reflectivity on said mechanical element, and providing a marking thereon with a laser, said marking comprising a plurality of areas having a second reflectivity, further comprising one of the following expedients;

a) prior to providing the mechanical element with said surface having first reflectivity, the step of providing the mechanical element with a substrate on which said surface is then provided, b) marking said areas having a second reflectivity such that said areas have a width which is generally constant in a direction parallel to the direction of movement of the mechanical element.

According to a third aspect of the invention we provide a mechanical element marked by a method according to the second aspect of the invention.

The apparatus according to the first aspect of the invention may comprise a mechanical element according to the third aspect of the invention.

An embodiment of the invention will now be described with reference to the accompanying drawings wherein FIG. 1 is a schematic view of a fluid operable ram incorporating an embodiment of the invention FIG. 2 is a cross-section on line 2—2 of FIG. 1

FIG. 5 shows an example schematic arrangement of decoding means

FIG. 6a is an example of part of an intermediate signal

FIG. 6b is the intermediate signal of FIG. 6a after passing through the decoding means of FIG. 5

FIG. 7 is a flowchart showing an example of steps performed by a decoding means according to one aspect of the invention

Figure 1:
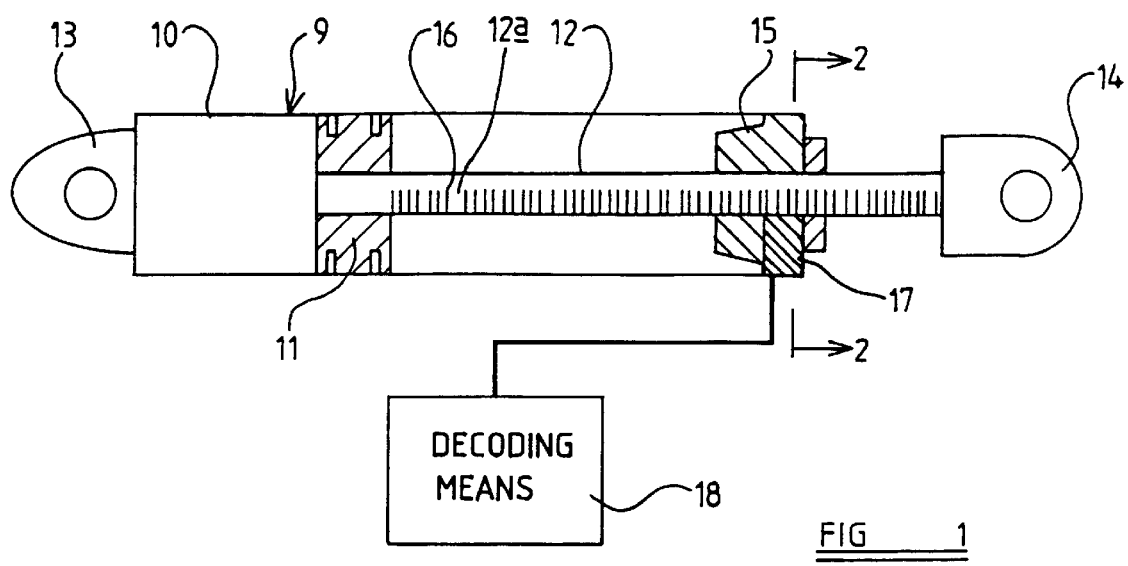

Referring now to FIG. 1, a fluid operable ram is shown at 9 comprising a cylinder 10 having a piston 11 received in the cylinder 10 and attached to a piston rod 12. In the present example, the mechanical element comprises the piston rod 12, although it will be clear that the invention may be used with any suitable mechanical element. The cylinder 10 and piston rod 12 may be attached to other mechanical devices as desired by ears 13 and 14 respectively. One end of the cylinder 10 is sealed by a cylinder end cap 15. The piston rod 12 has a surface 12a marked with an optically readable marking 16 disposed on the surface 12a. A reading means 17 is disposed with the cylinder end cap 15 and is connected to decoding means indicated generally at 18. The optically readable marking 16 comprises a series of code elements each encoding a numerical value based on the position of the code element along the length of the rod 12, in a fashion to be described hereinafter.

Figure 2:
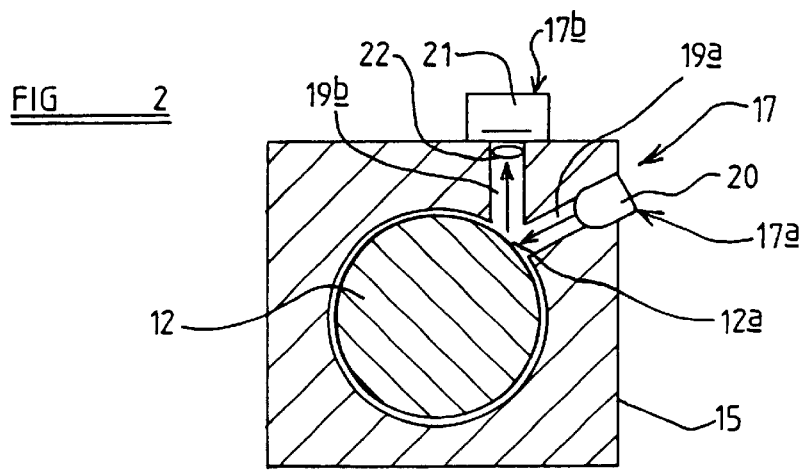

The reading means 17 is shown in FIG. 2 Optical pathways 19a, 19b are provided in the end cap 15. An illumination means 17a comprising a number of light emitting diodes (LEDs) 20 transmits light down pathway 19a such that it falls upon a part of the optically readable markings 16 provided on the surface 12a of the piston rod 12. The optical pathway 19b is disposed such that light reflected from the surface 12a of the piston rod 12 travels along the pathway 19b and is focused onto the detector array 21 preferably by a lens 22. The LEDs 20 are disposed to provide even illumination of the part of the optically readable markings 16 viewed by the detector array 21 in order to simplify subsequent processing. The reading means 17 is required to be compact to enable it to be mounted in or near the end cap 15 as shown.

Figure 3:
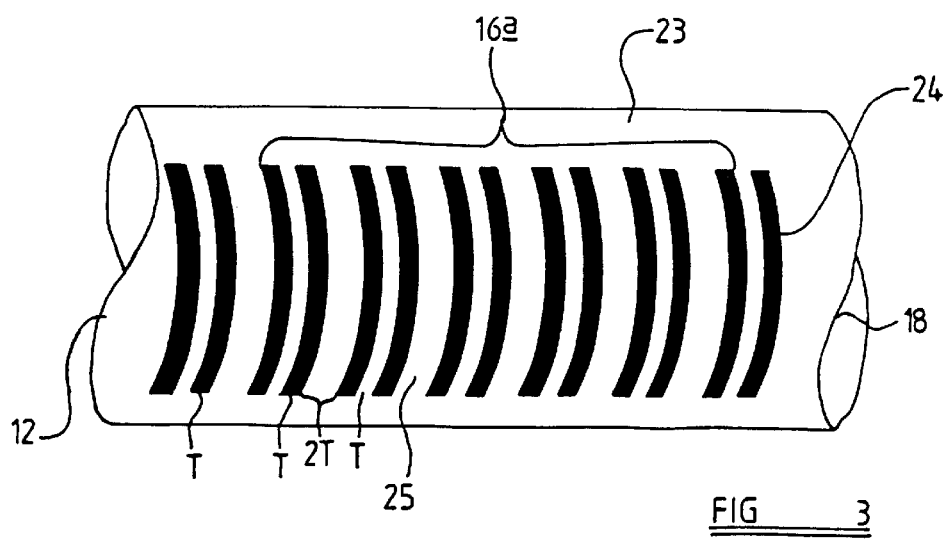
FIG. 3 is a enlarged view of part of FIG. 1

An example of the encoding scheme is shown in FIG. 3. This shows one code element 16a, that is, a distinguishable part of the optically readable marking 16 encoding one numerical value in binary digits (bits). The numerical value indicates the position of the code element 16a on the rod 12. The code element 16a comprises a part 23 of the surface 12a of the piston rod 12 having a first reflectivity upon which are marked areas 24 having a second, lower, reflectivity. The areas 24 have a fixed width T. Disposed between the areas 24 are spaces 25. The width of each space 25 encodes a bit; where the width of a space 25 is 2T, this indicates a bit having the value "1" and where a space 25 has a width of 1T, this indicates a bit having the value "0". The code element 16a shown in FIG. 3 thus encodes the binary sequence 1010101010.

The marking may comprise a series of successive, discrete, code elements, in which case end markers may be included, for example, a width of 4T between a pair of adjacent areas 24. In this case each successive code element 16a may encode a value increasing with its position along the length of the rod. The size of the code element 16a dictates the resolution with which the rod position may be measured.

More preferably, the marking uses a pseudorandom binary sequence to encode the positional information. Pseudorandom sequences and methods generating pseudorandom sequences are well known. The advantage is that for any pseudorandom sequence of order N, any N-bit segment of the sequence occurs only once, i.e. each N-bit segment is unique. The marking hence comprises a series of unique, overlapping code elements of length N bits. Where a sequence of order N is used as the pseudorandom sequence, the length in bits of the sequence is given by $2^N-1$, and the sequence produced will contain $2^{N-1}$ bits having the value "1" and $2^{N-1}-1$ bits having the value "0". The total length of the marking 16 for such a sequence where '1' bits have a width of 2T, '0' bits have a width of T and the digits are separated by marks of width T will be $(2^{N+1}+2^{N-1}+1)T$. The use of a pseudorandom sequence has the advantage that a single track of markings can used to provide absolute position sensing with a resolution of the width of one binary digit. The resolution of the system can be selected by varying the length T and the order of the pseudorandom binary sequence, and the marking is scaleable for different lengths of mechanical elements by altering the order of the pseudorandom binary sequence.

The resolution of the position information can be further increased to the width of one detector of the detector array by calculating a fine position as discussed below.

The linear detector array 21 comprises a semi-conductor device comprising an array of discrete photo-detectors arranged in a line disposed parallel to the longitudinal axis of the rod 12. Each photo-detector produces a signal whose voltage is proportional to the amount of light which falls upon the photo detector. The intermediate signal from the detector array comprises a series of voltage values, each value corresponding to the signal of one of the photo-detectors. Each discrete value may be referred to by the position (hereinafter referred to as its 'detector number') of its producing detector in the array. The focusing means 22 and width T of the areas 24 is preferably selected such that the light from any given region of the surface 12a having a width T falls upon at least two photo-detectors. It is essential to ensure that the maximum size code frame 16a, (in an example having 8 bits, a code frame 16a encoding the value 11111111), will fit within the length of the detector array. The resolution to which the position is measurable and the width T are hence variable depending on the resolution of the detector array. The use of the detector array 21 provides a compact detector means with a high density of photo detectors.

Most preferably, the detector can detect more bits than the minimum needed to identify a unique code element. In case of the pseudorandom binary sequence, the additional bits can be used for the purpose of error checking.

Figure 4:
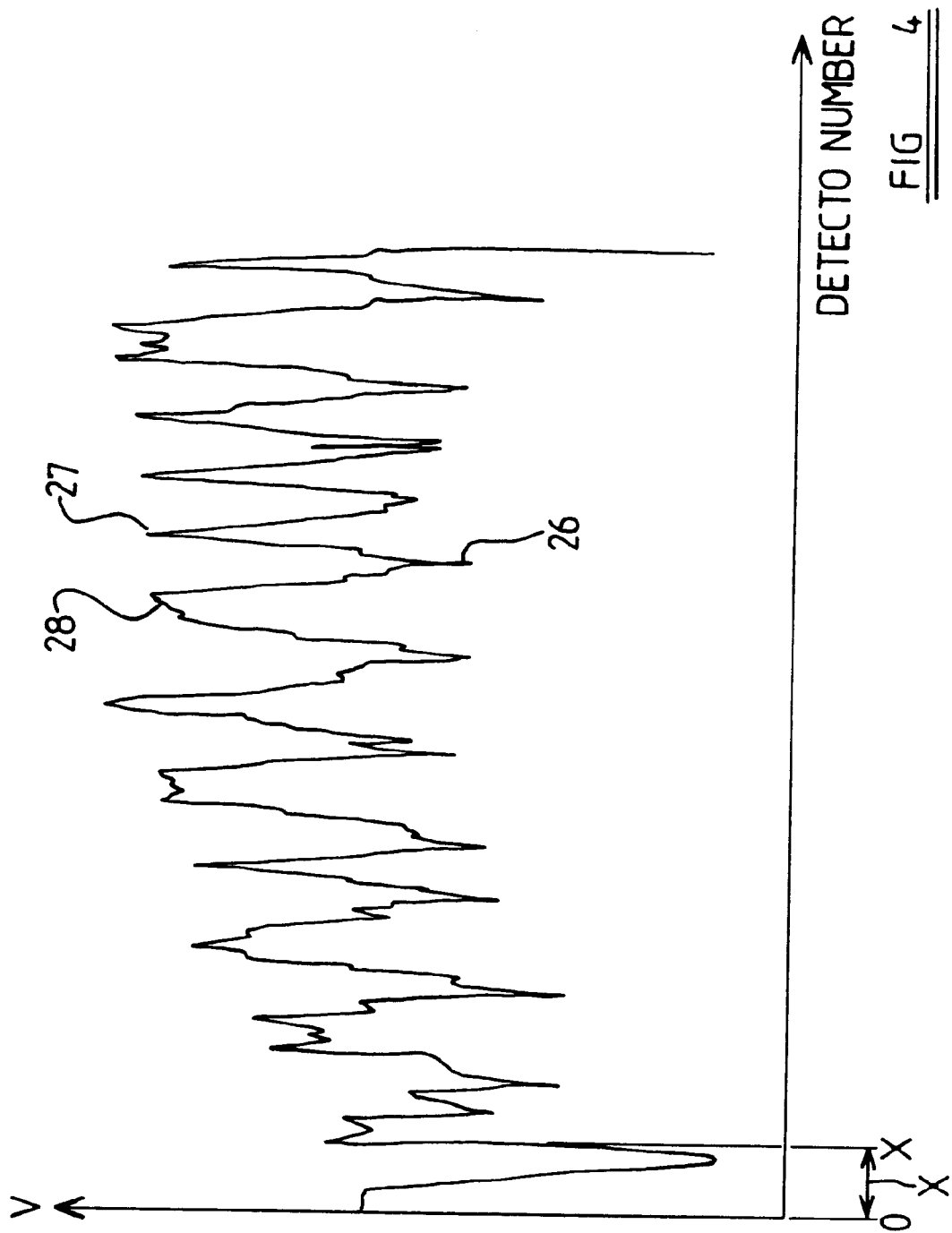
FIG. 4 is a graphical representation of an intermediate signal

An example of the intermediate signal from the detector array 21 is shown in FIG. 4. The areas 24 appear as minima 26, whilst spaces 25 corresponding to binary "0" digits appear as narrow peaks 27 and spaces 25 corresponding to binary 1" digits appear as wide peaks 28.

A possible configuration for a decoding means is shown in FIG. 5 in schematic form. The intermediate signal is supplied by the detector array 21 in FIG. 2 on line 30 to a DC voltage level shift 31, which is controllable by a micro-controller 32 to vary the voltage of the second output 30. The voltage-shifted intermediate signal is supplied on line 33 from the DC voltage level shift 31 to a discriminator 34 which compares the value of the intermediate signal with a threshold voltage. Where the value of the intermediate signal is above the threshold voltage, the discriminator 34 generates a signal voltage of +5 volts, and where the value of the intermediate signal is below the threshold voltage, generates a signal voltage of 0 V. The discriminator 34 thus converts the intermediate signal into a waveform comprising 5 volt "marks" which correspond to the spaces 25 and 0 volt "spaces" which correspond to the areas 24. The waveform is then supplied on line 35 to the micro-controller 32 which extracts the encoded numerical value and converts it to the output transmitted on line 37. The intermediate signal on line 33 is read by the micro-controller 32 and a voltage shift adjustment signal is provided accordingly on a line 36 to the DC voltage level shift 31 to maintain the midpoint between the maximum and minimum values of the intermediate signal coincident with the threshold voltage of the discriminator 34.

The decoding means may alternatively comprise a analogue to digital converter and a microcontroller, computer or other suitable programmable device provided with suitable software to decode the intermediate signal. The analogue to digital convertor converts the intermediate signal into a series of digitised valves which is passed to the microcontroller. The software in the present example then performs the steps of first smoothing the digitised intermediate signal by taking an average of adjacent values of the intermediate signal to smooth out any high frequency components in the intermediate signal, and then identifying those values of the intermediate signal which correspond to the midpoints of a transition between a minimum and a maximum by comparing the rate of change between the signal from adjacent detectors. Each transition corresponds to an edge of an area 24. The step of identifying subsequent transitions can be speeded up, once a first transition has been identified. Since it is clear that a transition from high to low must be followed by a transition from low to high a given distance later, since the edges of each area 24 are a known distance apart, and that any transition from low to high be followed by a transition from high to low at either the given distance or twice the given distance later, corresponding to a space 25 of width T or 2T respectively, only those values of the intermediate signal likely to correspond to a transition need be tested by the software. Since it will be known how many detectors correspond to the width T of the areas 24, the likely spacing of the transitions in terms of the number of detectors will be known.

The steps performed by the decoding means are shown in the flow chart of FIG. 7. The intermediate signal is passed to a discriminator which detects transitions and notes the detector numbers of the values of the intermediate signal which correspond to transitions. The sequence of detector numbers each corresponding to a transition is then decoded to extract the binary sequence by identifying the bits from the widths of the separations between transitions. The number of bits corresponding to a word of the pseudorandom sequence is extracted from the binary sequence and is validated to ensure it is a valid part of the pseudorandom sequence. Once it has been confirmed as valid, the position of the mechanical element can be found from a look-up table, in which each word of the pseudorandom binary sequence is matched against the corresponding position of the rod.

Such a method gives the position of the mechanical element to within resolution of the width of one binary digit of the pseudorandom sequence marked on the mechanical element. A fine position can then be calculated by identifying the detector number X of the detector on which the first transition falls in FIG. 4. The position of the detector X thus gives the start of the binary sequence from a given reference point in this case, the first detector 0 of the array. Since, as discussed above, it is known how many detectors correspond to a width T of the pseudorandom sequence, by counting the number of detectors between X and 0 a fine position of the piston rod can be calculated to within the width of one detector of the detector array.

Figure 8:
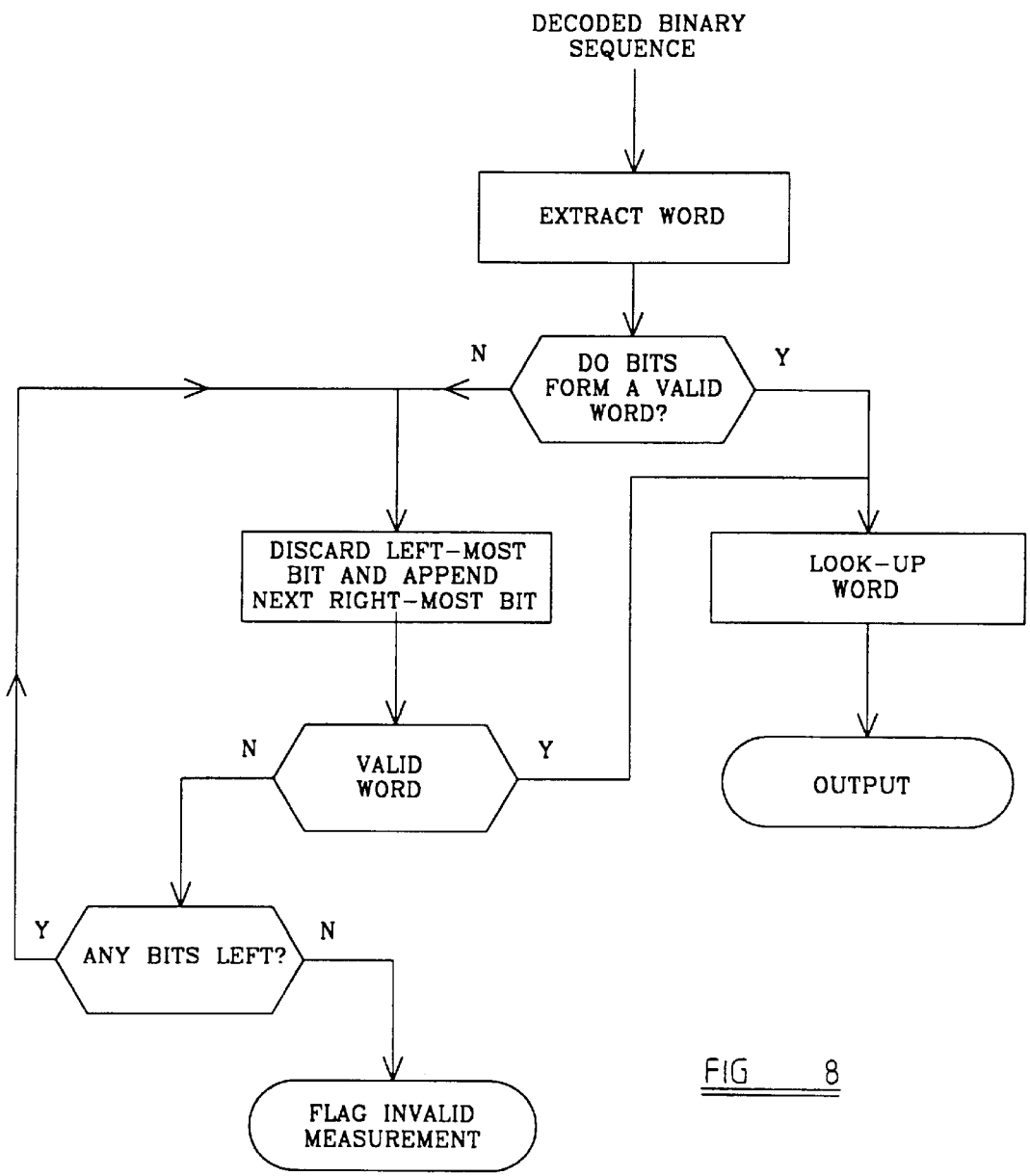
FIG. 8 is a flowchart showing an example of error checking steps performed by a decoding means according to one aspect of the invention

A simple flowchart for the validation stage is shown in FIG. 8. The identified bits are checked to see whether they form a valid word. If not, the left most bit of the word can be discarded and the next bit of the binary sequence appended to provide a new right most bit. The resulting word is again tested to see whether it forms a valid word. If it does, the word is looked up on the lookup table to provide a position as described above. If not, the process of discarding the left most bit and appending a new right most bit is repeated. If all bits are tested without producing a valid word, then an invalid measurement is flagged. The validation stage can thus identify errors caused by damage to the marking or the rod surface or electrical noise in the detection means and decoding means.

It is desirable that the decoding means identify where an invalid bit has occurred, e.g. due to erosion of an area 24, for example by deducing which must be the invalid bit from adjacent valid readings. If the position of such an invalid bit can be identified, the correct value of the bit can be identified and used in subsequent measurements.

Figure 9:
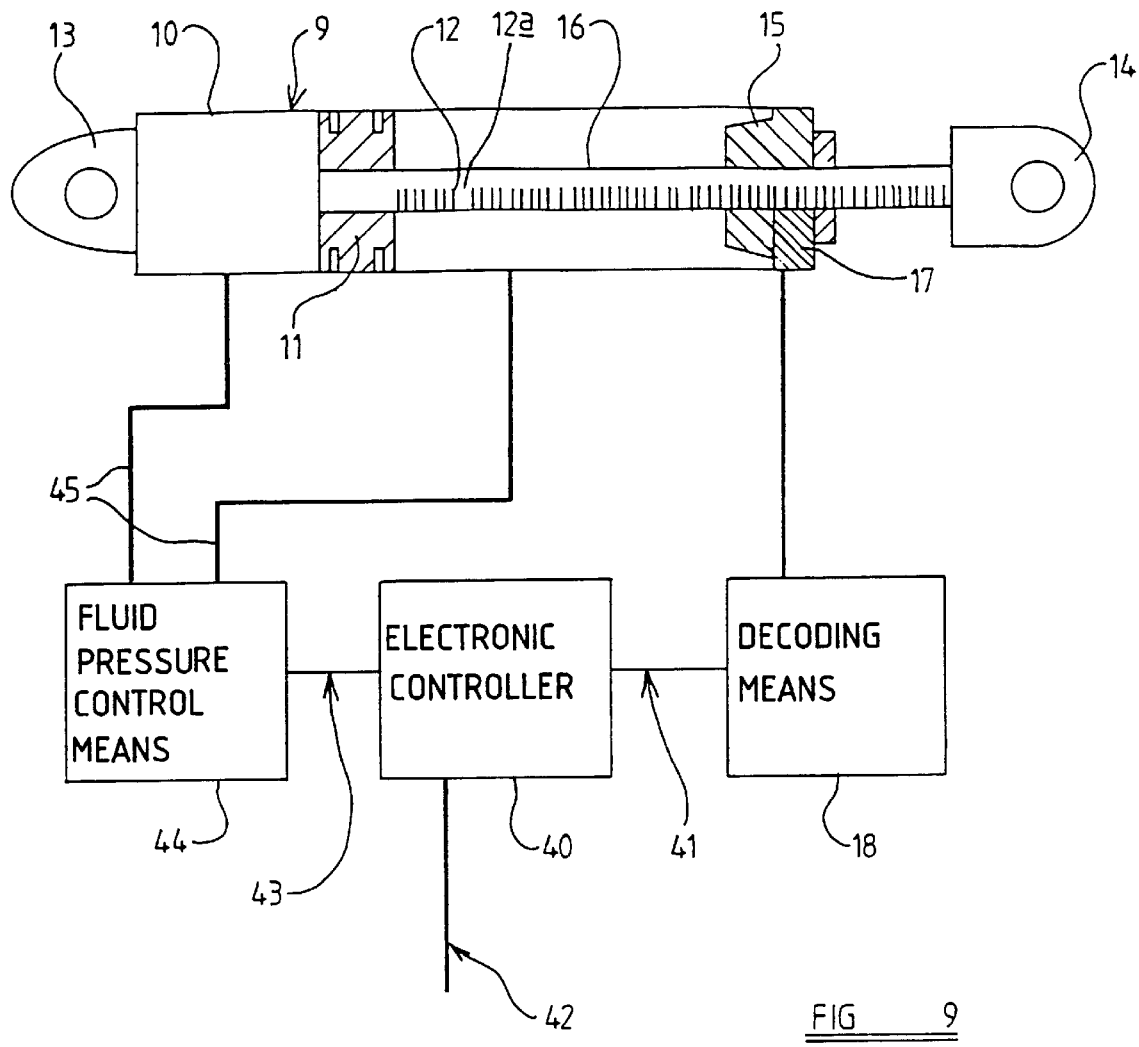
FIG. 9 is a schematic arrangement of an electronic feedback control system incorporating an embodiment of the invention.

Such an apparatus for determining the position of a mechanical element could be used in a servo system operable to control the mechanical element in response to the output signal of the apparatus. In the present example, suitable valve means may be provided whereby supply of fluid pressure to the cylinder is electronically controlled. A possible schematic arrangement is shown in FIG. 9. A fluid operable ram a like that shown in FIG. 1 comprises a reading means 17 and decoding means 18 as hereinbefore described. The output from the decoding means 18 is passed on line 41 to an electronic controller 40. Signals from other sensors or control means as desired may also be passed to the electronic controller 40 on line 42. The electronic controller 40 may then operate a fluid pressure control means 44 comprising, for example, a solenoid valve by sending a signal on line 43 to control the supply of fluid on lines 45 to the ram 9 in response to the positional information from the decoding means 18 and sensor information on line 42. The rod 12 will move accordingly and its new position will be detected by the reading means 17 and decoding means 18 and passed to the electronic controller 40.

The requirements of the optically readable marking 16 are that it should encode positional information such that the absolute displacement of the rod can be determined to a desired resolution, be tolerant of errors introduced by loss of areas 24 and minimise the number of areas 24 required on the rod surface. It is also desirable that the markings be durable and corrosion resistant, and as far as possible not impair the corrosion resistance of the rod itself. Either expedient may be used where it is desired to resist impairment of the corrosion resistance of the mechanical element.

According to the first expedient of the invention, the optically readable marking is provided on a mechanical element once it has been ground to the diameter required. In the present example, the mechanical element is steel and the appropriate parts of it are first coated with a bronze substrate. The mechanical element is preferably ground or wet polished before coating to have a surface finish of 0.8 µm or less. The bronze substrate has a thickness in the range 0.038 to 0.051 mm and comprises 88% to 92% copper and 8% to 12% tin. After coating, the bronze substrate should show no sign of porosity, and is polished to achieve a surface finish of 0.2 to 0.4 µm. A chromium surface is deposited on the bronze at a rate of 0.001 mm/hour by a conventional electrodeposition technique to provide a surface 12a having a first reflectivity. The surface may have micro cracks at approximately 400 cracks/linear cm minimum. The final chrome thickness may be varied for different components depending on the final use of the component. Other suitable techniques or parameters may be used as desired.

The chromium is then removed by scanning the desired areas with a laser to produce exposed areas of bronze having a second, lower, reflectivity. The laser is scanned around a portion of the rod circumference to provide a circumferential mark in a plane perpendicular to the axis of the piston rod 12. The rod 12 is moved a slight distance axially and another region scanned until an area 24 having the desired width has been generated. This process is repeated for each area 24 as desired. The area 24 may alternatively be formed by partially removing or discolouring the chromium without entirely remaining the chromium, particularly where expedient (b) of the invention is provided where it is envisaged that no or another substrate may be provided.

In the present example, the laser used is a Q-switched Nd-YAG with a continuous wave power of 70 watts operated in Q mode at a power of 600 watts. The beam diameter was 4 mm and the focal length 137 mm with a scanning speed of 70 mm per second. For a rod having a circumference of 40 mm, each area 24 was scanned to extend around 5.7 mm of the rod circumference and to have a width of 0.5 mm.

This method produces a durable corrosion resistant marking, the bronze substrate resisting any impairment of the corrosion resistance of the rod arising from the laser marking of the chromium. Although nickel is conventionally used as a substrate when depositing chromium onto steel since it is generally regarded as providing better corrosion resistance than a bronze substrate, contrary to expectations a nickel substrate was found to be less effective at countering any impairment of the corrosion resistance caused by the laser making of the chromium. In particular, it is difficult to control the laser power so that the chrome is marked but so that the laser does not significantly affect the substrate and the mechanical element. Alternatively, where only chromium is provided, the laser opens corrosion paths through micro cracks in the chromium. A bronze substrate provides a corrosion resistant substrate which is highly reflective to the marking laser. The laser power need may not be controlled so accurately, since once the chrome surface has been marked, the laser light is subsequently reflected by the bronze substrate, making it less likely that the laser will burn through the substrate to the mechanical element below or open corrosion paths through to the element. Further, the use of bronze, which has a very different reflectivity to chrome, provides areas 24 of high contrast. The marking method provides a readable marking which lasts for a predetermined lifetime without degradation. The marking are also sufficiently durable not to be easily eroded by normal use or damaged by accidental impact. Where the mechanical element is provided with a conventional seal which wipes the chrome surface, any dirt or oil on the element will serve to heighten contrast between the surface and areas since the areas will be slightly recessed and will accumulate some oil or dirt, thus lowering their reflectivity further.

The method can be used on induction hardened steel, as well as other grades of steel including non-induction hardened steel.

The use of constant width markings according to the second expedient of the invention also resists impairment of the corrosion resistance caused by laser marking of the surface. If only chromium is provided, it is desirable that the marking does not penetrate through the chromium to the mechanical element, requiring control of the depth and penetration and hence power of the laser. Where a substrate is provided, it may still be desirable that the marking does not penetrate the chromium, or alternatively that the marking does not result in significant penetration or heating of the substrate. When a mark is formed by a laser on a mechanical element, the amount of heating caused to the element is dependent on the size of the mark, which further affects the depth of penetration of the laser. By making the marks of constant width, the heating of the mechanical element is normally constant and the depth of penetration will be more easily controlled, since the effect of making the mark will be known without having to calibrate the laser power for different sizes of mark. The method can be used in addition to or separate from the method of providing a bronze substrate described above to provide corrosion resistance. The marking may be formed using the technique described hereinbefore.

Further, as described above, since the width of the areas is constant and the width of the space between areas is either the width of one or two areas, the detection of transitions in the intermediate signal can be sped up, thus accelerating the decoding process.

The reading means comprises no moving parts, and does not interfere with the movement of the element. The position measurement is taken directly from the rod and not from a piece of apparatus actuated to the element. This means that the position measurement is not affected by mechanical deficiencies such as backlash between the ram and the apparatus, or in the reading means itself. The reading means also does not add any extra moving parts to the ram which would be subject to wear.

Other encoding or marking means may be used as desired. While in the present example a piston rod has been marked, it will be clear that such a method of determining position optically would be appropriate for any other mechanical element subject to axial or other movement. The illumination means and detector means are mounted in the end cap of the cylinder and are therefore mechanically protected and screened from electro-magnetic disturbances, as well as being relatively compact.

It will be apparent that the present invention may be used on any mechanical element as desired, and in particular a marking may be provided by any suitable technique as desired. Either or both expedients of the invention may be used where it is desired to resist impairment of the corrosion resistance of a mechanical element.

The features disclosed in the foregoing description, or the following claims, or the accompanying drawings, expressed in their specific forms or in terms of a means for performing the disclosed function, or a method or process for attaining the disclosed result, as appropriate, may, separately, or in any combination of such features, be utilised for realising the invention in diverse forms thereof.

What is claimed is:

1. A mechanical element comprising an optically readable marking, the optically readable marking comprising a surface and a plurality of areas, the surface having a first reflectivity and the plurality of areas having a second reflectivity, wherein a substrate is disposed between the mechanical element and the surface, and wherein the surface comprises chromium and wherein the substrate comprises bronze, and further wherein each of the plurality of areas comprises an exposed area of the substrate.

2. A mechanical element according to claim 1 wherein the substrate is resistant to corrosion.

3. A mechanical element according to claim 1 wherein the substrate is more resistant to laser marking than is the surface.

4. A mechanical element according to claim 1 wherein the bronze comprises 88% to 92% copper, and 12% to 8% tin.

5. A mechanical element according to claim 1 wherein the bronze substrate has a thickness in the range of 0.038 mm to 0.051 mm.

6. A mechanical element according to claim 1 wherein the bronze has a surface finish in the range of 0.2 to 0.4 microns.

7. A mechanical element according to claim 1 wherein a part of the mechanical element to be provided with the substrate has a surface finish of less than 0.8 microns.

8. A mechanical element according to claim 1 wherein the first reflectivity is greater than the second reflectivity.

9. A mechanical element comprising an optically readable marking, the optically readable marking comprising a surface having a first reflectivity and a plurality of areas having a second reflectivity, each of the areas having a width, the width of each of the areas being generally the same in a direction parallel to a direction of movement of the mechanical element, and wherein adjacent areas are separated by a distance, the distance being variable, and further wherein a binary digit is indicated by the distance between two of the areas.

10. A mechanical element according to claim 9 wherein the marking comprises a plurality of code elements, each of the code elements comprising a plurality of the areas.

11. A mechanical element according to claim 10 wherein each of the code elements encodes a different numerical value in binary digits.

12. A mechanical element according to claim 11 wherein each of the code elements encodes a unique number.

13. A mechanical element according to claim 12 wherein each of the code elements comprises a unique part of a pseudorandom binary sequence.

14. A mechanical element according to claim 9 wherein each of the areas all have generally the same surface area.

15. An apparatus for determining the position of a movable mechanical element wherein the mechanical element comprises an optically readable marking, the optically readable marking comprising a surface having a first reflectivity and a plurality of areas having a second reflectivity, wherein a substrate is disposed between the mechanical element and the surface, wherein the surface comprises chromium and the substrate comprises bronze, and wherein the areas comprise exposed areas of the substrate, the apparatus comprising reading means to provide an output dependent on the position of the mechanical element, the reading means comprising illuminating means, detector means and decoding means.

16. An apparatus according to claim 15 wherein the illuminating means comprises a light emitting diode.

17. An apparatus according to claim 16 wherein the detector means is disposed to detect light from the illuminating means reflected from the surface and from the areas, the detector means comprising a detector which provides a signal having a first value within a first range when light from a part of the surface is reflected onto the detector means and having a second value within a second range when light from one of the areas is reflected onto the detector means.

18. An apparatus according to claim 17 wherein the detector means comprises an array having a plurality of detectors.

19. An apparatus according to claim 18 wherein the array provides an intermediate signal to the decoding means, the intermediate signal comprising a signal from each of the plurality of detectors.

20. An apparatus according to claim 19 wherein the decoding means comprises electronic means to decode the intermediate signal from the detector means to provide the output.

21. An apparatus according to claim 20 wherein the marking comprises a plurality of code elements, each of the plurality of code elements comprising a group of the areas, wherein the decoding means comprises means to detect a detector signal of the intermediate signal corresponding to a transition, the transition corresponding to an edge of one of the areas, and means to identify a plurality of binary digits from the separation of a plurality of the transitions.

22. An apparatus according to claim 21 wherein the encoding means comprises means to identify a code element from the plurality of binary digits and provide the output indicating the position of the mechanical element dependent on the code element.

23. An apparatus according to claim 22 wherein the decoding means further comprises means to identify the detector of the detector array on which a selected one of said transitions falls.

24. An apparatus according to claim 23 further comprising focusing means to focus light reflected from the surface of the mechanical element or from the areas onto the detector means.

25. An apparatus according to claim 24 wherein the mechanical element comprises a piston rod of a fluid operated ram.

26. An apparatus for determining the position of a movable mechanical element wherein the mechanical element comprises an optically readable marking, the optically readable marking comprising a surface and a plurality of areas, the surface having a first reflectivity and the plurality of areas having a second reflectivity, each of the areas having a generally equal width measured in a direction parallel to a direction of movement of the mechanical element, wherein adjacent areas are separated by a distance, the distance being variable, and wherein a binary digit is indicated by the distance, the apparatus comprising reading means to provide an output dependent on the position of the mechanical element, said reading means comprising illuminating means, detector means and decoding means.

27. An apparatus according to claim 26 wherein the illuminating means comprises a light emitting diode.

28. An apparatus according to claim 27 wherein the detector means is disposed to detect light from the illuminating means reflected from the surface and from the areas, the detector means comprising a detector which provides a signal having a first value within a first range when light from a part of the surface is reflected onto the detector means and having a second value within a second range when light from an area is reflected onto the detector means.

29. An apparatus according to claim 28 wherein the detector means comprises an array having a plurality of detectors.

30. An apparatus according to claim 29 wherein the array provides an intermediate signal to the decoding means, the intermediate signal comprising a signal from each of the detectors.

31. An apparatus according to claim 30 wherein the decoding means comprises electronic means to decode the intermediate signal from the detector means to provide the output.

32. An apparatus according to claim 31 wherein the marking comprises a plurality of code elements, each of the plurality of code elements comprising a plurality of the areas, wherein the decoding means comprises means to detect a detector signal of the intermediate signal corresponding to a transition, the transition corresponding to an edge of each of the areas, and means to identify a plurality of binary digits from a separation between a plurality of the transitions.

33. An apparatus according to claim 32 wherein the encoding means comprises means to identify a code element from the binary digits and to provide the output, the output indicating the position of the mechanical element dependent on the code element.

34. An apparatus according to claim 33 wherein the decoding means further comprises means to identify the detector of the detector array on which a selected one of the transitions falls.

35. An apparatus according to claim 34 further comprising focusing means to focus light reflected from the surface or from the areas onto the detector means.

36. An apparatus according to claim 35 wherein the mechanical element comprises a piston rod of a fluid operated ram.

37. An apparatus according to claim 26 wherein each of the areas have substantially the same surface area.

38. A method of marking a mechanical element comprising providing the mechanical element with a substrate and providing a surface on the substrate, wherein the substrate comprises bronze and the surface comprises chromium, and providing a marking thereon, the marking comprising a plurality of areas, each of the areas having a reflectivity, the method comprising the step of marking each of the areas by removing a portion of the surface to expose a portion of the substrate.

39. A method according to claim 38 wherein the step of removing the portion of the surface comprises using a laser.

40. A method of marking a mechanical element comprising the steps of providing a surface on the mechanical element, the surface having a first reflectivity, the mechanical element including a marking, the marking comprising a plurality of areas, each of the plurality of areas having a second reflectivity, marking the areas such that the areas each have generally the same width in a direction parallel to a direction of movement of the mechanical element, and wherein a binary digit is indicated by a distance between two of the areas.

41. A method according to claim 40 wherein each of the areas have generally the same surface area.

42. A method according to claim 41 wherein the step of marking the areas comprises using a laser to form the areas.

* * * * *